(12) United States Patent
Nishioka et al.

(10) Patent No.: US 7,923,254 B2
(45) Date of Patent: Apr. 12, 2011

(54) METHOD FOR STUDYING, DETERMINING OR EVALUATING PHARMACOLOGICAL ACTIONS OF A TEST SUBSTANCE ON AN SART STRESSED ANIMAL

(75) Inventors: Kusuki Nishioka, Tokyo (JP); Tomohiro Kato, Tokyo (JP); Hiroki Fujisawa, Osaka (JP)

(73) Assignee: Nippon Zoki Pharmaceutical Co., Ltd., Osaka (JP)

( * ) Notice: Subject to any disclaimer, the term of this patent is extended or adjusted under 35 U.S.C. 154(b) by 82 days.

(21) Appl. No.: 12/310,746

(22) PCT Filed: Sep. 5, 2007

(86) PCT No.: PCT/JP2007/067291
§ 371 (c)(1),
(2), (4) Date: May 26, 2009

(87) PCT Pub. No.: WO2008/029836
PCT Pub. Date: Mar. 13, 2008

(65) Prior Publication Data
US 2009/0272649 A1    Nov. 5, 2009

(30) Foreign Application Priority Data
Sep. 6, 2006  (JP) ................................ 2006-240924

(51) Int. Cl.
*G01N 33/48* (2006.01)
(52) U.S. Cl. .......................................... 436/63; 436/86
(58) Field of Classification Search ................. None
See application file for complete search history.

(56) References Cited

U.S. PATENT DOCUMENTS

| 2006/0051376 A1 | 3/2006 | Nishioka |
| 2006/0263388 A1 | 11/2006 | Nishioka |
| 2007/0218037 A1 | 9/2007 | Nishioka |
| 2008/0194038 A1 | 8/2008 | Nishioka et al. |

FOREIGN PATENT DOCUMENTS

| WO | WO 2004/039383 A1 | 5/2004 |
| WO | WO 2006/095674 A1 | 9/2006 |

OTHER PUBLICATIONS

Hata et al., "Changes in CNS Levels of Serotonin and Its Metabolite in SART-Stressed (Repeatedly Cold-Stressed) Rats", Japan J. Pharmacol., vol. 56, pp. 101-104, 1991.
Soeller et al., "Neurotransmission: Harnessing Fusion Machinery at the Synapse", Trends Neurosci., vol. 17, No. 8, pp. 344-348, 1994.
Ishida, "Proteomics Ni Okeru Tanpakushitsu Hatsugen Differential Kaiseki—Keiko Hyoshiki Nijigen Difference Denki Eido: Ettan™ DIGE", Clinical Testing, vol. 47, No. 11, pp. 1269-1276, 2003, (Untranslated Japanese Document).
Nishioka, "Sen'ikintsusho No Kenkyu No Shinpo", Inflammation & Immunology, vol. 12, No. 6, pp. 2-6, 2004, (Untranslated Japanese Document).
Kawamura et al., "Neurotropin No Chintsu Sayo Kijo—Gekosei Totsu Yokusei-kei O Chushin Ni Shite-", Brain 21, vol. 4, No. 2, pp. 71-76, 2001, (Untranslated Japanese Document).
Hata et al., "Plasma Catecholamine Levels in SART-Stressed Rats and Effects of Drugs on Stress-Induced Alteration in Plasma and Brain Catecholamine Levels", J. Auton. Pharmacol., vol. 11, pp. 15-25, 1991.

*Primary Examiner* — John D Ulm
(74) *Attorney, Agent, or Firm* — Oliff & Berridge, PLC

(57) ABSTRACT

A method for studying, determining or evaluating a pharmacological action of a test substance, the method including subjecting the brain tissue of an SART stressed animal administered with the test substance to an expression proteome analysis, where expression changes of NSF (N-ethylmaleimide sensitive fusion protein), which is or is not modified after translation, in the SART stressed animal administered with the test substance as compared with an SART stressed animal to which a test substance is not administered is used as an index.

10 Claims, No Drawings

METHOD FOR STUDYING, DETERMINING OR EVALUATING PHARMACOLOGICAL ACTIONS OF A TEST SUBSTANCE ON AN SART STRESSED ANIMAL

TECHNICAL FIELD

The present invention relates to a method for study, determination or evaluation of pharmacological actions, particularly an effect on fibromyalgia, an analgesic effect or an antistress effect of a test substance by means of administering the test substance to a SART stressed animal and then subjecting the brain tissue thereof to an expression proteome analysis.

BACKGROUND ART

Fibromyalgia is a disease in which chronic and systemic strong pain or, even partially, chronic pain within a broad area is a main symptom and the pain is sometimes noted not only in muscle tissues but also in the skin. The fibromyalgia is often accompanied not only with systemic chronic pain as such but also with sense of fatigue, malaise, depression, anxiety, muscle tightness in the morning, muscle stiffness and sleep disorders. It is also sometimes accompanied with headache, facial pain, dysgnosia (lapse of memory, lack of concentration), gastrointestinal complaint (visceral pain, disorder of digestive system and flatulence), pollakiuria, diarrhea, constipation, dysmenorrhea, etc.

Prevalence rate of fibromyalgia to the general population in the United States has been reported to be 3.4% for women and 0.5% for men. It occurs frequently in females of about 25 to 50 years age and about 80% of the patients are females. The situation in Japan is believed to be nearly the same as that in the United States. In fibromyalgia, subjective symptoms are variegated while its objective opinion are not too much except its characteristic systemic pressure pain. Even when not only image diagnosis such as MRI and CT but also pathological test of muscular pain sites and various immunological, virological and endocrinological tests are carried out, abnormal observation is rarely noted. For example, unlike rheumatic arthritis, no edema is observed and, in spite of the fact that the index in blood showing the degree of inflammation such as erythrocyte sedimentation rate and CRP is within a normal range, patients complain pain in broad areas of extremity and body trunk.

With regard to a diagnostic method therefor, the classification criteria proposed by the American College of Rheumatologyin 1990 have been used throughout the world at present. In the criteria, the case where pain is noted in all of the five areas of upper, lower, right and left halves of the body where the umbilical region is a cardinal point and also vertebral and sternal part and said pain continues at least for three months or the case where, when a mild load of 4 kg is applied to the stipulated 18 areas throughout the body, pain is noted in 11 or more areas is diagnosed as fibromyalgia.

At present, cause and mechanism of onset of fibromyalgia are presumed to be psychological elements such as stress, viral infection, heredity, abnormality in immunity and in neurotransmitters although they have not been clarified yet. Fibromyalgia is a disease which is quite different from many common pain diseases caused by injury of biological tissues or nociceptive stimulus which may cause injury and no related pathological observation is noted in the painful site.

In the treatment of fibromyalgia, most of anti-inflammatory and analgesic drugs such as nonsteroidal anti-inflammatory drugs (NSAIDs) which have been frequently used for the treatment of common pain are ineffective. Although various drugs such as muscle relaxants, opioid analgesics and anti-anxiety agents have been tried, their efficacy greatly varies among individuals and no significant effect is noted. Accordingly, at present, for the treatment of fibromyalgia, prescription of antidepressants or a combination thereof with NSAIDs, administration of local anesthetic or steroidal agent to painful site, massage, therapeutic exercise, sleep therapy, etc. have been merely applied. However, in any of the therapeutic agents and methods, difference in the therapeutic effect among individuals is big partly because the cause for fibromyalgia has not been specified yet, whereby no therapeutic method has been established yet.

As mentioned above, cause and mechanism of onset of fibromyalgia have not been clarified yet at present and, therefore, there has been a demand for a method of studying, determining or evaluating the substances which are effective for this disease.

An object of the present invention is to provide a method for study, determination or evaluation of a substance which is effective for fibromyalgia or pain diseases.

The present inventors have firstly paid their attention to the similarities between fibromyalgia and SART stressed animals.

SART stressed animals are the animals which are loaded with SART (specific alternation of rhythm in temperature) stress, in other words, a repetitive cold stress and mice, rats, guinea pigs and the like are able to be prepared. Method of preparation is able to be carried out in accordance with a method of Kita, et al. (Folia Pharmacologica Japonica, 71:195, 1975). For example, in the case of rats, temperature for breeding environment is changed at 24° C. and −3° C. every one hour from 10 a.m. to 5 p.m., then it is kept at 4° C. from 5 p.m. to 10 a.m. of the next morning. Thus, the repetitive cold stress is loaded by breeding for 4 days or more where water and feed are freely taken by them whereupon the SART stressed rats are prepared. The temperature setting of as low as −3° C. in the case of rats is changed to 4° C. for mice and to 0° C. for guinea pigs whereupon SART stressed mice and SART stressed guinea pigs are able to be prepared respectively.

In the SART stressed animals prepared as such, there have been known such characteristics that their pain threshold values lower due to the repeated cold stress (pain sensitivity), anxiety and depression are promoted, release of CRH (corticotropin-releasing hormone), noradrenaline and IL-1β is promoted and release of serotonin (5-HT) is suppressed. Body weight decreases as well.

On the other hand, it has been also known that, in the patients suffering from fibromyalgia, there are characteristics that pain threshold value lowers, anxiety and depression are promoted, release of CRH (corticotropin-releasing hormone), noradrenaline, substance P, IL-1β, IL-2, IL-6 and IL-8 is promoted and release of serotonin (5-HT) is suppressed. It has been found that, with regard to those respects, fibromyalgia has a common point with SART stressed animals.

In the meanwhile, it has been known already that, in SART stressed animals, an extract from inflamed tissues inoculated with vaccinia virus has an antistress action such as a suppressive action for lowering of pain threshold (pain sensitivity) (analgesic action), a suppressive action for promotion of release of CRH (corticotropin-releasing hormone), noradrenaline and IL-1β and for suppression of release of serotonin (5-HT) and a suppressive action for body weight decrease (*Kiso to Rinsho*, volume 15, No. 5, page 2459, 1981; Pharmacometrics (*Oyo Butsuri*), volume 32, No. 3, page 599, 1986; etc.). The titer determination of a pharmaceutical preparation that an extract from inflamed rabbit skin inoculated with vaccinia virus is an effective ingredient (trade name: Neurotropin) is conducted by means of analgesic effect test using the SART stressed animals, which is defined as a quantitative test therefor.

The preparation of an extract from inflamed rabbit skin inoculated with vaccinia virus is a very unique preparation which has been allowed to be used for a broad range of indications such as itch accompanied by skin diseases (such as eczema, dermatitis and urticaria), allergic rhinitis and secuelae of SMON (coldness, paresthesia/dysesthesia, pain, etc.) in addition to painful diseases such as low back pain, neck-shoulder-arm syndrome, symptomatic neuralgia, periarthritis scapulohumeralis, degenerative arthritis deformans and post-herpetic neuralgia. Injection preparations for hypodermic, intramuscular and intravenous uses and tablet preparations have been approved to manufacture as ethical drugs and put into the market. In recent years, clinical tests therefor have been carried out in the United States for RSD (reflex sympathetic dystrophy, CRPS-type 1) which is an intractable neuropathic pain.

It has been also found in recent years that the extract from inflamed tissues inoculated with vaccinia virus is effective for fibromyalgia (*Arthritis Res. Ther.*, 5 (Suppl. 3): S53, 170, 2003; etc.). The fact that the extract from inflamed tissues inoculated with vaccinia virus is effective for fibromyalgia is mentioned in the following Patent Document.

Patent Document 1: International Publication WO 2004/039,383

DISCLOSURE OF THE INVENTION

The present inventors have carried out intensive studies by paying their attention to the above-mentioned facts that SART stressed animals and patients suffering from fibromyalgia have common characteristics, and that an extract from inflamed tissues inoculated with vaccinia virus has an analgesic action to both of them, whose mechanism is believed to be improvement in lowering of function of the descending pain inhibitory system. As a result, they have invented a method of studying, determining or evaluating a pharmacological action, particularly an effect to fibromyalgia, an analgesic effect or an antistress effect of a test substance by administration of said test substance to SART stressed animals followed by subjecting the brain tissue thereof to an expression proteome analysis.

The present invention is to provide a method of studying, determining or evaluating a pharmacological action, particularly an effect to fibromyalgia, an analgesic effect or an antistress effect of a test substance by administration of said test substance to SART stressed animals followed by subjecting the brain tissue thereof to an expression proteome analysis whereby it is now possible to conduct investigation of substances effective for fibromyalgia and painful diseases, determination or evaluation of the effect thereof or analysis of a target protein of said substances.

BEST MODE FOR CARRYING OUT THE INVENTION

An extract from inflamed tissues inoculated with vaccinia virus is prepared in such a manner that vaccinia virus is inoculated to an animal, the inflamed tissues are ground, an extracting solvent is added thereto, the tissue pieces are removed, a treatment for removal of protein is conducted followed by adsorbing with an adsorbent and the adsorbed component is eluted.

An extract from inflamed tissues inoculated with vaccinia virus is manufactured, for example, by the following steps.

(a) Inflamed skin tissues of rabbits, mice, etc. by inoculation of vaccinia virus are collected, the inflamed tissues are ground, an extracting solvent such as water, aqueous phenol, physiological saline solution or phenol-added aqueous glycerol is added and the mixture is filtered or centrifuged to give an extracted fluid (filtrate or supernatant liquid).

(b) The above extracted fluid is adjusted to an acidic pH and heated for deproteinization. The deproteinized solution is made alkaline and heated, and then filtered or centrifuged.

(c) The resulting filtrate or supernatant fluid is made acidic and adsorbed with an adsorbent such as active carbon or kaolin.

(d) An extracting solvent such as water is added to the above adsorbent, the mixture is adjusted to an alkaline pH and the adsorbed component is eluted whereupon an extract from inflamed tissues inoculated with vaccinia virus is able to be prepared.

Each of the above steps will now be illustrated in more detail as follows.

About (a):

Inflammatory skin tissues where smallpox occurred by inoculation of vaccinia virus to rabbits such as domestic rabbits are collected and ground and an extracting solvent in 1 to 5-fold amount was added thereto to prepare an emulsified suspension. As to the extracting solvent, distilled water, physiological saline solution, weakly acidic to weakly basic buffer, etc. may be used and a stabilizer such as glycerol, a bactericide/antiseptic agent such as phenol, a salt such as sodium chloride, potassium chloride and magnesium chloride, etc. may be appropriately added thereto. It is also possible that, at that time, a treatment by means of freeze-thawing, ultrasonic wave, cell membrane dissolving enzyme, surfactant, etc. is conducted to destroy the cell tissues whereby the extraction is made easy.

About (b):

The resulting milky extract is filtered, centrifuged or the like to remove the tissue pieces and then a deproteinizing treatment is carried out. The deproteinizing operation is able to be carried out by a known method which has been commonly done and it is possible to apply a method such as a heating treatment, a treatment using a protein modifier such as acid, base, urea or an organic solvent (e.g., guanidine and acetone), an isoelectric precipitation and a salting out. After that, a common method for removal of impurities such as filtration using filter paper (cellulose, nitrocellulose, etc.), glass filter, Celite, Seitz filter, etc., ultrafiltration or centrifugation is carried out whereby the insoluble protein separated out therefrom is removed.

About (c):

The extract containing the effective component as such is adjusted to acidic or, preferably, to pH 3.5 to 5.5 using an acid such as hydrochloric acid, sulfuric acid or hydrobromic acid and an adsorbing operation with an adsorbent is carried out. As to the adsorbent which is able to be used, active carbon, kaolin, etc. may be exemplified and the adsorbent is added to the extract followed by stirring or the extract is passed through a column filled with the adsorbent so that the effective component is able to be adsorbed with said adsorbent. When an adsorbent is added to the extract, the solution is removed by filtration, centrifugation, etc. whereby an adsorbent with which an effective component is adsorbed is able to be prepared.

About (d):

In the elution (detachment) of the effective component from the adsorbent, it is able to be achieved in such a manner that an eluting solvent is added to the above adsorbent, elution is conducted at room temperature or with appropriate heating or with stirring and the adsorbent is removed by a common method such as filtration or centrifugation. As to the eluting solvent used therefor, a basic solvent such as water, methanol, ethanol, isopropanol or an appropriate mixture thereof which is adjusted to a basic pH is able to be used. Preferably, water where pH is adjusted to 9 to 12 is used.

More specific manufacturing method is mentioned, for example, in the above Patent Document 1.

Examples

Firstly, brain tissue samples of SART stressed animals were prepared as follows.

(1) Animals

Male rats of Wistar strain of six weeks age were loaded with SART stress to prepare SART stressed rats. The rats were freely fed with feed and tap water and loaded for five days and, on the sixth day, they were released from the stress load and subjected to the experiment.

(2) Extract from Inflamed Tissues Inoculated with Vaccinia Virus

As to an extract from inflamed tissues inoculated with vaccinia virus, there was used an extract prepared from the inflammatory skin of rabbit to which vaccinia virus as manufactured according to Example 2 of the above-mentioned Patent Document 1 which was adjusted to 20 NU/mL (an extract from inflamed rabbit skin inoculated with vaccinia virus). NU is stipulated by $ED_{50}$ value of analgesic effect when an SART stressed mouse which is a chronic stressed animal where pain threshold value is lower than that in normal animal was used and a test according to a modified Randall-Selitto method was conducted. 1 NU is the activity showing 1 mg of an analgesic activity-containing component of the extract from inflamed rabbit skin inoculated with vaccinia virus when $ED_{50}$ value is 100 mg/kg.

(3) Administration of an Extract from Inflamed Rabbit Skin Inoculated with Vaccinia Virus An extract from inflamed rabbit skin inoculated with vaccinia virus was intraperitoneally administered consecutively in the dose of 200 NU/kg body weight to the above SART stressed rat from the initial day when SART stress was loaded (a SART stressed group administered with test substance). A physiological saline solution was administered in the same schedule to a normal control group and to an SART stressed control group. The administered liquid amount was made 10 ml per kg body weight. Group organizations were made as follows. Thus, they were the normal control group (n=5), the SART stressed control group (n=10) and the SART stressed group administered with the test substance (n=10).

(4) Measurement of Pain Threshold Value

The pain threshold value was measured by a test according to a modified Randall-Selitto method using a measuring apparatus for analgesic effect for pressed stimulation. Thus, pressed stimulation was applied to the right hind paw of a rat with a predetermined pressing velocity and the pressing weight (g) by which the animal shows escape reaction or squeaking reaction was measured as a pain threshold value.

From the above, the following result was achieved.

(1) Changes in Body Weight

In body weight of the SART stressed control group, a significant suppression of body weight increase was noted from the first day of initiation of loading of stress as compared with the normal control group. There was no change in the body weight of the SART stressed group administered with a test substance as compared with the SART stressed control group.

(2) Effect of an Extract from Inflamed Rabbit Skin Inoculated with Vaccinia Virus on Lowering of Pain Threshold Value of SART Stressed Rat When SART stress was loaded for five days, the pain threshold value significantly lowered as compared with the normal control group. When the pain threshold value was measured after 30 minutes from the final administration in the SART stressed group to which a test substance was added, a significant improvement was observed as compared with the SART stressed control group.

(3) Samples

After the lowering of the pain threshold value by loading with SART stress and the analgesic effect of an extract from inflamed rabbit skin inoculated with vaccinia virus were able to be confirmed as mentioned above, cerebrum, mesencephalon, cerebellum, diencephalon, pons/medulla, posterior horn and dorsal root ganglion were collected from the brain tissues of each of the groups. A sample from four rabbits in each group was homogenized by a cell-dissolving buffer (30 mmol/L Tris hydrochloride, 20 mol/L thiourea, 7 mol/L urea and 4% CHAPS; pH: 8.5) [CHAPS: 3-[(3-cholamidopropyl) dimethylammonio]propanesulfonic acid] under cooling with ice using a Polytlon homogenizer. The tissue homogenate was quickly cooled using liquid nitrogen and stored by freezing at −80° C. until use.

After that, proteins which vary their expression amount in central and peripheral nerves of the SART stressed animal were detected by a fluorescence-labeled two-dimensional difference gel electrophoresis (2D-DEGE) method using the samples prepared by the above method and those proteins were identified using a matrix-aided laser detached ion time-of-flight mass spectrometer (MALDI-TOF/MS). Details are as follows.

(1) Reagents

All of the reagents used in the above two-dimensional electrophoresis were in the grade being manufactured by the manufacturer which was designated by GE Healthcare Bioscience (old name: Amersham Bioscience). With regard to urea and thiourea used for the cell dissolving buffer and the swelling buffer, they were used after shaking with Amberlite (an ion-exchanging resin) whereby the decomposed products were removed by being adsorbed therewith so as to prevent the undesirable affection of the decomposed products on the experimental system. For preparing the reagents, ultrapure water (Milli-Q water) was used.

(2) Fluorescence-Labeled Two-Dimensional Difference Gel Electrophoresis (2D-DIGE) Method Protein concentration of the sample prepared by the above method was quantified using a calibration curve prepared from bovine serum albumin by a Bradford method. That was used as a sample for the two-dimensional electrophoresis and, for the analysis of changes in expressed amount of protein, a 2D-DIGE method was used.

(3) Labeling Reaction Using a Fluorescence-Labeled Reagent (Cy Dye)

A cell-dissolving buffer was used for preparing a sample whereby the protein concentration therein was made 2 or 5 mg/mL and the liquid property was confirmed to be within a range of pH 8.0 to 9.0. Each of the all samples to be measured was mixed in the same amount and the prepared one was used as an internal standard. The internal standard protein sample (50 μg) was placed in a microtube, 1 μL of a Cy Dye DIGE Fluor minimal dye labeling solution (a Cy Dye pigment was diluted with anhydrous dimethylformamide to an extent of 400 pmol/μL) was added thereto and the mixture was stirred and allowed to stand in ice in a dark place for 30 minutes so that the protein was labeled. The internal standard sample was labeled with a Cy 2 pigment while the protein sample was labeled with a Cy 3 or Cy 5 pigment. A 10 mmol/L lysine solution (1 μL) was added and allowed to stand for 10 minutes in ice in a dark place to stop the labeling reaction. Each of the samples labeled with Cy 2, Cy 3 and Cy 5 was placed in a microtube and mixed and the mixture was used for a first dimensional electrophoresis.

(4) First Dimensional Electrophoresis

With regard to the first dimensional electrophoresis, an isoelectric focusing using an IPG precast gel (Immobiline Drystrip) and an isoelectric focusing system (IPGphor) of Amersham Bioscience was carried out. Those where strip length was 24 cm and pH range was pH 4-7 L, 4.5-5.5 L, 5.3-6.5 L and 6-9 L were used.

In the case of a strip where pH was 4-7 L, 4.5-5.5 L and 5.3-6.5 L, swelling and addition of the sample were conducted at the same time. A swelling buffer containing the sample (2 mol/L thiourea, 7 mol/L urea, 4% CHAPS, 1.2% DeStreak Reagent and 0.5% IPG Buffer) (450 μL) was placed on a 24-cm strip holder, then an IPG strip was placed thereon, swelling was conducted for 10 hours and then electrophoresis of 130,000 to 180,000 VHr was conducted where maximum per strip was 50 μA and 8,000 V at the highest.

In the case of a strip of pH 6-9 L for separation of protein of the basic side, better result is achieved when a sample is added after the swelling and, therefore, an IPG strip was swollen for not shorter than 10 hours in a swelling tray on which a swelling buffer (450μL) containing no sample was placed and, after that, a sample was added using a sample cup whereupon electrophoresis of 960,000 VHr was conducted where maximum per strip was 50μA and 8,000 V at the highest.

An operation after addition of the sample was carried out under the condition where light is shielded as much as possible and the strip where migration was finished was stored at −80° C. until the second dimensional electrophoresis.

(5) Second Dimensional Electrophoresis

The second dimensional electrophoresis was carried out by means of a sodium dodecylsulfate-polyacrylamide gel electrophoresis (SDS-PAGE; acrylamide concentration: 12.5%) in a size of 24 cm×20 cm with 1 mm thickness. An equilibrating buffer A (50 mmol/L Tris hydrochloride, 6 mol/L urea, 30% glycerol, 2% SDS and 1% dithiothreitol; pH 8.8) was added to the strip where the electrophoresis was finished followed by shaking for 15 minutes, then a change to an equilibrating buffer B (50 mmol/L Tris hydrochloride, 60 mol/L urea, 30% glycerol, 2% SDS and 2.5% iodoacetamide; pH 8.8) was done and shaking was conducted for 15 minutes more. The second dimensional electrophoresis was conducted immediately after completion of the equilibration. The migration was conducted at 10° C. with 2 W/gel under the state where light was shielded until the front end of the migration reached to the position of 5 to 10 mm from the lower end of the gel.

(6) Analysis

The gel where the migration was finished was taken out from a migration vessel, shielded from light and, under the state of being sandwiched with glass plates, it was immediately subjected to incorporation of fluorescent images of Cy 2, Cy 3 and Cy 5 (excitation wavelength/fluorescent wavelength: Cy 2: 488 nm/520 nm, Cy 3: 532 nm/580 nm, Cy 5: 633 nm/670 nm) using a Typhoon 9400 variable image analyzer (an apparatus for fluorescent image analysis). Six sheets of gel (gel image numbers: 18) for each nerve tissue were subjected to detection of spots, matching and statistic analysis using a DeCyder Differential Analysis Software. Comparisons were conducted between normal control group and SART stressed control group and between the SART stressed control group and the SART stressed group administered with a test substance and the spots where difference in expressed amounts was not less than 1.5-fold and the result of t-test was $p<0.05$ were selected.

(7) Analysis of Phosphorylated Protein

In order to confirm the influence of posttranslational modification, labeling of total protein using a fluorescent labeling reagent (Cy Dye) and staining of phosphorylated protein using a phosphorylating protein staining reagent (Pro-Q Diamond) were carried out for the same gel. A sample (50 μg) was labeled with Cy 2, mixed with 450 μg of a sample which was not labeled and the mixture was subjected to a two-dimensional electrophoresis in the same manner as above. After completion of the migration, a staining operation was conducted under shielding from light so that fading of Cy Dye and Pro-Q Diamond did not happen.

The gel was taken out from the glass plates, dipped in a fixing solution (50% methanol and 10% trichloroacetic acid) and fixed by gently shaking for 1 hour at room temperature, then a fixing solution was exchanged followed by gently shaking overnight and a fixing solution was further exchanged followed by gently shaking for 1 hour to fix. The fixed gel was washed with a secondary distilled water for 15 minutes for four times, 500 mL of a staining solution was added, the mixture was shaken for 2 hours to stain and, after that, a decolorizing solution (20% acetonitrile and 50 mmol/L sodium acetate; pH 4.0) was added thereto and the mixture was washed for 30 minutes for three times. The gel was subjected to a measurement using a Typhoon 9400 variable image analyzer at excitation wavelength 633 nm/fluorescent wavelength 670 nm for Cy 5 and at excitation wavelength 532 nm/fluorescent wavelength 580 nm for Pro-Q.

(8) Identification of Protein Using MALDI-TOF/MS

A tissue homogenate corresponding to 500 μg in terms of the amount of protein was added as a sample and subjected to the two-dimensional electrophoresis the same as above.

Staining of total protein in the gel was conducted using a SYPRO Ruby Protein Gel and Blot Stain kit in accordance with the protocols thereof. The gel where the migration was finished was taken out from the glass plates, dipped in 500 mL of a fixing solution (10% methanol and 7% acetic acid) and gently shaken at room temperature for not shorter than 5 hours under shielding from light to fix. After fixation, 500 mL of a staining solution was added and the mixture was gently shaken at room temperature for not shorter than 5 hours under shielding from light to stain. After that, 500 mL of a decolorizing solution (10% methanol and 6% acetic acid) was added and the mixture was gently shaken at room temperature for 1 to 2 hour(s) under shielding from light to decolorize. The gel was measured using a Typhoon 9400 variable image analyzer at excitation wavelength 457 nm/fluorescent wavelength 610 nm. With regard to the gel after the staining, an aimed spot was picked using a BioRad Spot Cutter and was analyzed.

The result was as follows.

(1) Analysis of Changes in Protein Expression within a Range of pH 4 to 7

In all of the collected tissues, a fluorescence-labeled two-dimensional difference gel electrophoresis (2D-DIGE) analysis was conducted within a range of pH 4 to 7.

(1-1) Cerebrum

As a result of the analysis, no spot where the difference in the expressed amounts was 1.5-fold or more and $p<0.05$ in a t-test was found in a comparison between the normal control group and the SART stressed control group and a comparison between the SART stressed control group and the SART stressed control group administered with a test substance. Hereinafter, the difference in the expressed amounts of spots was evaluated by the same test standard.

(1-2) Diencephalon

No spot where the difference in the expressed amounts was noted was found in the comparison between the normal control group and the SART stressed control group and between the SART stressed control group and the SART stressed control group administered with a test substance.

(1-3) Mesencephalon

In a comparison between the normal control group and the SART stressed control group, an increase was noted in 5 spots and no spot where decrease was noted was found in the SART stressed control group. In the SART stressed control group and the SART stressed group administered with a test substance, an increase was noted in one spot and a decrease was noted in 4 spots in the group administered with a test substance.

(1-5) Pons

In a comparison between the normal control group and the SART stressed control group, an increase was noted in 6 spots and a decrease was noted in 4 spots in the SART stressed control group. In the SART stressed control group and the SART stressed group administered with a test substance, an increase was noted in 3 spots while no spot where decrease was noted was found in the group administered with a test substance.

(1-5) Medulla Oblongata

In a comparison between the normal control group and the SART stressed control group, no spot where increase was noted was found and a decrease was noted in one spot in the SART stressed control group. In the SART stressed control group and the SART stressed group administered with a test substance, no spot where increase was noted was found and an increase was noted in one spot in the group to which a test substance was administered.

(1-6) Cerebellum

In a comparison between the normal control group and the SART stressed control group, an increase was noted in 5 spots and a decrease was noted in 9 spots in the SART stressed control group. In the SART stressed control group and the SART stressed group administered with a test substance, there was no spot where there was a difference in the expressed amounts.

(1-7) Posterior Horn

In a comparison between the normal control group and the SART stressed control group, an increase was noted in one spot and no spot where a decrease was noted was found in the SART stressed control group. In the SART stressed control group and the SART stressed group administered with a test substance, an increase was noted in one spot and a decrease was noted in one spot in the group to which a test substance was administered.

(1-8) Dorsal Root Ganglion

In a comparison between the normal control group and the SART stressed control group, an increase was noted in one spot and no spot where a decrease was noted was found in the SART stressed control group. In the SART stressed control group and the SART stressed group administered with a test substance, there was no spot where there was a difference in the expressed amounts.

Spot numbers where changes were found in the experiments hereinabove are shown in Table 1.

TABLE 1

| | pH 4 to 7 | | | |
|---|---|---|---|---|
| | Normal Control Group (INT) vs. SART stressed Control Group (SART) | | SART stressed Control Group (SART) vs. SART stressed Group Administered with Test Substance (DRUG) | |
| | INT < SART | INT > SART | SART < DRUG | SART > DRUG |
| Cerebrum | 0 | 0 | 0 | 0 |
| Diencephalon | 0 | 0 | 0 | 0 |
| Mesencephalon | 5 | 0 | 1 | 4 |
| Pons | 6 | 4 | 3 | 0 |
| Medulla oblongata | 0 | 1 | 0 | 1 |
| Cerebellum | 5 | 9 | 0 | 0 |
| Posterior horn | 2 | 0 | 1 | 1 |
| Dorsal root ganglion | 1 | 0 | 0 | 0 | n = 4, t-test (2) Analysis of Changes in Protein Expression within Narrow pH Ranges (pH 4.5 to 5.5 and pH 5.3 to 6.5)

A DIGE within narrower ranges (pH 4.5 to 5.5 and pH 5.3 to 6.5) was conducted for mesencephalon, pons and cerebellum where changes in plural spots were noted within a pH range of 4 to 7 whereby reconfirmation of the result obtained in pH 4 to 7 and detection of new spots were tried.

(2-1) Mesencephalon

In the normal control group and the SART stressed control group within a pH range of 4.5 to 5.5, an increase was noted in 14 spots and a decrease was noted in 6 spots in the SART stressed group. In the SART stressed control group and the SART stressed group administered with a test substance, an increase was noted in one spot and a decrease was noted in 14 spots in the group administered with a test substance. In the normal control group and the SART stressed control group within a pH range of 5.3 to 6.5, an increase was noted in 7 spots and a decrease was noted in 2 spots in the SART stressed control group. In the SART stressed control group and the SART stressed group administered with a test substance, an increase was noted in 2 spots and a decrease was noted in 6 spots in the group administered with a test substance.

In the spots where changes were noted within a range of pH 4 to 7 in the mesencephalon, significant changes in 1.5-fold or more were noted even within ranges of pH 4.5 to 5.5 and pH 5.3 to 6.5 except one spot whereby the reproducibility of the experiment was able to be confirmed.

(2-2) Pons

Within a range of pH 4.5 to 5.5, no spot where there was a difference in expressed amounts was found between the normal control group and the SART stressed control group and between the SART stressed control group and the SART stressed group administered with a test substance. Within a range of pH 5.3 to 6.5, between the normal control group and the SART stressed control group, an increase was noted in one spot and a decrease was noted in one spot in the SART stressed control group. Between the SART stressed control group and the SART stressed group administered with a test substance, an increase was noted in 2 spots and a decrease was noted in one spot in the group administered with a test substance.

In the pons, the spot where changes were able to be detected within a range of pH 4 to 7 was unable to be confirmed within the ranges of pH 4.5 to 5.5 and pH 5.3 to 6.5.

(2-3) Cerebellum

Within a range of pH 4.5 to 5.5, between the normal control group and the SART stressed control group, an increase was noted in 3 spots and a decrease was noted in 12 spots in the SART stressed control group. Between the SART stressed control group and the SART stressed group administered with a test substance, an increase was noted in 2 spots and a decrease was noted in one spot in the group administered with a test substance. Within a range of pH 5.3 to 6.5, between the normal control group and the SART stressed control group, an increase was noted in 2 spots and a decrease was noted in 7 spots in the SART stressed control group. Between the SART stressed control group and the SART stressed group administered with a test substance, an increase was noted in one spot and no spot was found where an increase was noted in the group administered with a test substance.

With regard to the spots where changes were noted within a range of pH 4 to 7 in the cerebellum, significant changes to an extent of not less than 1.5-fold were noted except 2 spots even within the ranges of pH 4.5 to 5.5 and pH 5.3 to 6.5 whereby a reproducibility of the experiment was able to be confirmed.

(3) Analysis of Changes in Protein Expression within a Range of pH 6 to 9

Result of a DIGE analysis in the cerebrum and the dorsal root ganglion within a range of pH 6 to 9 was as shown below.

(3-1) Cerebrum

Between the normal control group and the SART stressed control group and between the SART stressed control group and the SART stressed group administered with a test substance, no spot where there was a difference in expressed amounts was found.

(3-2) Dorsal Root Ganglion

Between the normal control group and the SART stressed control group and between the SART stressed control group and the SART stressed group administered with a test substance, no spot where there was a difference in expressed amounts was found.

Numbers of spots where changes were found in the experiments within a narrow pH range and a basic pH range are shown in Table 2.

TABLE 2

| | pH 4.5 to 5.5 | | | |
| --- | --- | --- | --- | --- |
| | Normal Control Group (INT) vs. SART stressed Control Group (SART) | | SART stressed Control Group (SART) vs. SART stressed Group Administered with Test Substance (DRUG) | |
| | INT < SART | INT > SART | SART < DRUG | SART > DRUG |
| Mesencephalon | 14 | 6 | 1 | 14 |
| Pons | 0 | 0 | 0 | 0 |
| Cerebellum | 3 | 12 | 2 | 1 |

| | pH 5.3 to 6.5 | | | |
| --- | --- | --- | --- | --- |
| | Normal Control Group (INT) vs. SART stressed Control Group (SART) | | SART stressed Control Group (SART) vs. SART stressed Group Administered with Test Substance (DRUG) | |
| | INT < SART | INT > SART | SART < DRUG | SART > DRUG |
| Mesencephalon | 7 | 2 | 2 | 6 |
| Pons | 1 | 1 | 2 | 1 |
| Cerebellum | 2 | 7 | 1 | 0 |

TABLE 2-continued

| | pH 6 to 9 | | | |
| --- | --- | --- | --- | --- |
| | Normal Control Group (INT) vs. SART stressed Control Group (SART) | | SART stressed Control Group (SART) vs. SART stressed Group Administered with Test Substance (DRUG) | |
| | INT < SART | INT > SART | SART < DRUG | SART > DRUG |
| Cerebrum | 0 | 0 | 0 | 0 |
| Dorsal Root Ganglion | 0 | 0 | 0 | 0 | n = 4, t-test in all cases (4) Analysis of Phosphorylation of Mesencephalon Sample It has been said that a proteome analysis is able to find the influence of posttranslational modification and is advantageous as compared with other means. Accordingly, phosphorylation of protein was confirmed in a mesencephalon sample. Total protein was pre-labeled with Cy 5 and subjected to a two-dimensional electrophoresis, protein which is phosphorylated is stained with ProQ Diamond, image was obtained by each fluorescent wavelength and it was confirmed whether the protein was phosphorylated.

(5) Identification of Protein where Changes were Confirmed

Two-dimensional electrophoresis was carried out for samples of mesencephalon, pons and cerebellum and the spot was picked, digested in gel and analyzed by an MALDI-TOF/MS.

As mentioned above, it was confirmed by a proteome analysis using 2D-DIGE that, in SART stressed animals, plural proteins were changed in mesencephalon, pons and cerebellum.

Advantages of a proteomics analysis are that even posttranslational modification which is unable to be confirmed in a genetic level is able to be confirmed. In a DIGE analysis, protein which is subjected to a posttranslational modification such as phosphorylation, saccharification and cleavage is able to be confirmed as a different spot and, therefore, confirmation whether the spot is phosphorylated protein was carried out by means of staining with Pro-Q Diamond. When Cy Dye labeling and Pro-Q Diamond staining are combined, it was now possible to confirm whether the spot which was able to be confirmed of changes by DIGE was phosphorylated.

As a result of identification by means of MALDI-TOF/MS for the protein where changes were able to be confirmed, the proteins which were able to be identified were the following 22. They were CRMP-2, CRMP-4, Munc-18-1, Complexin 1, Complexin 2, Synapsin 2, PGP 9.5 (Protein gene product 9.5), Alpha-synuclein, Erk 2 (MAPK), Ser/Thr protein kinase PAK 2, TOLLIP, Actin related protein 2/3 sub 2, Actin related protein 2/3 sub 4, Tubulin alpha, Regucalcin (SMP 30), eIF5A, Aldehyde dehydrogenase, Succinyl CoA ligase, Creatine kinase, Citrate synthase, ATP synthase and NSF (N-ethylmaleimide sensitive fusion protein). Table 3 shows the expressed amounts of spots of each of the identified proteins in the SART stressed control group (SART) and the SART stressed group administered with a test substance (Drug) where the expressed amount of the normal control group was 1.

TABLE 3

| Names of Proteins | Mesencephalon | | Pons | | Cerebellum | |
|---|---|---|---|---|---|---|
| | SART | SART + Drug | SART | SART + Drug | SART | SART + Drug |
| CRMP-2 | 1.9* | 0.79+ | 0.64* | 0.85 | 0.26* | 0.39 |
| CRMP-4 | 0.58* | 0.95+ | 0.64* | 0.8 | | |
| Munc-18-1 | 2.9* | 0.94+ | | | 0.30* | 0.51 |
| Complexin 1 | | | | | 1.6* | 1.4 |
| Complexin 2 | | | | | 1.5* | 1.4 |
| Synapsin 2 | | | | | 1.5* | 1.3 |
| Protein Gene Product 9.5 | | | 0.64* | 0.76 | | |
| Alaph-synuclein | | | 1.9* | 1.4 | | |
| Erk 2 (MAPK) | 1.3* | 1.2 | | | | |
| Ser/Thr protein kinase PAK 2 | | | | | 1.8* | 1.5 |
| TOLLIP | | | | | 0.14* | 0.19 |
| Actin related protein 2/3 sub 2 | 1.4* | 1.1 | | | | |
| Actin related protein 2/3 sub 4 | 1.30 | 0.93+ | | | | |
| Tubulin alpha | 1.9* | 0.79+ | | | 0.63* | 0.74 |
| Regucalcin (SMP 30) | 0.63* | 1.2+ | | | | |
| eIF5A | | | 2.0* | 1.4 | | |
| Aldehyde dehydrogenase | 1.4 | 0.8+ | | | | |
| Succinyl CoA ligase | 1.6* | 1.4 | | | | |
| Creatine kinase | 1.3* | 1.1 | | | | |
| Citrate synthase | 1.3* | 1.1 | | | | |
| ATP synthase | | | | | 0.69* | 0.81 |
| NSF | 3.2* | 0.85 | | | | |

Calculated as INT = 1
*p < 0.05 (vs INT, t-test)
+p < 0.05 (vs SART, t-test)

(6) Analysis of Identified Proteins

Among those identified proteins, a more detailed investigation was conducted for CRMP-2, CRMP-4, Munc-18-1 and NSF which showed changes by the SART stress load in the mesencephalon, and the changes were suppressed by administration of a test substance, and for Complexin 1/2 which showed changes by the SART stress loading in cerebellum.

(A) When the amount of mRNA of CRMP-2 in mesencephalic central gray matter was measured using a real-time PCR, changes in the amount of mRNA were unable to be confirmed by SART stress load and by administration of a test substance for SART stress load and it was shown that there was no affection during the transcription stage. Therefore, a mesencephalon homogenate was subjected to an electrophoresis using a polyacrylamide gel, transcribed to a PVDF membrane and detected using an anti-CRPM-2 antibody whereupon there was no change in the concentration of the band recognized by the anti-CRMP-2 antibody and it was suggested that, in the two-dimensional electrophoresis, changes which are able to be confirmed such as posttranslational modification took place. In order to confirm that, transcription to a PVDF membrane was conducted from the gel separated by the two-dimensional electrophoresis and detection was done using an anti-CRMP-2 antibody whereupon spot of CRMP-2 was also found at the position for higher molecular weight than the spot where changes were confirmed in 2D-DIGE. From such a result, it was suggested that the spot where changes were confirmed in 2D-DIGE is a cleavage-type CRMP-2 produced by cleavage of a part of CRMP-2.

(B) When the amount of mRNA of CRMP-4 in mesencephalic central gray matter was measured using a real-time PCR, changes in the amount of mRNA were also unable to be confirmed by SART stress load and by administration of a test substance for SART stress load in the case of CRMP-4 as well and it was shown that there was no affection during the transcription stage. Therefore, a mesencephalon homogenate was subjected to an electrophoresis using a polyacrylamide gel, transcribed to a PVDF membrane and detected using an anti-CRPM-4 antibody whereupon there was no change in the concentration of the band recognized by the anti-CRMP-4 antibody and it was suggested that, in the two-dimensional electrophoresis, changes which are able to be confirmed such as posttranslational modification took place. In order to confirm that, transcription to a PVDF membrane was conducted from the gel separated by the two-dimensional electrophoresis and detection was done using an anti-CRMP-4 antibody whereupon there were detected plural spots which were nearly in the same molecular weight as the spots where changes were confirmed by 2D-DIGE and which were different in isoelectric point whereby the possibility of posttranslational modification was predicted. Concentrations of those spots decreased in the acidic side and increased in the basic side due to SART stress load and such changes were suppressed by administration of the test substance. Since phosphorylation has been known as a posttranslational modification which changes the isoelectric point of protein, that was compared with a gel image stained with ProQ Diamond and it was found that the spots in acidic side were phosphorylated while those in basic side was not phosphorylated. From such a result, it was suggested that a decrease in a phosphorylated CRMP-4 due to SART stress load was found by 2D-DIGE.

(C) When the amount of mRNA of Munc-18-1 in a mesencephalic central gray matter was measured using a real-time PCR, changes in the amount of mRNA were also unable to be confirmed by SART stress load and by administration of a test substance for SART stress load in the case of Munc-18-1 as well and it was shown that there was no affection during the transcription stage. Therefore, a mesencephalon homogenate was subjected to an electrophoresis using a polyacrylamide gel, transcribed to a PVDF membrane and detected using an antibody which recognizes the amino acids 58-70 of Munc-18-1 whereupon a band which is newly recognized by the anti-Munc-18 antibody by an SART stress load was confirmed at the low molecular weight side and it was suggested that a posttranslational modification such as cleavage took place. In order to confirm that, transcription to a PVDF membrane from the gel separated by a two-dimensional electrophoresis was carried out and detection was conducted using the anti-Munc-18 antibody whereupon, in addition to the spots where changes were confirmed in 2D-DIGE, plural spots were also found at the high molecular weight side. Further, when detection was tried using an antibody which recognizes the amino acids 580 to 594 at C-terminal of Munc-18-1, the spots at the high molecular weight side were detected while the spots where changes were confirmed by 2D-DIGE were not detected. From those results, it was suggested that the spots found in 2D-DIGE were those where C-terminal was scissored from Munc-18-1, and also the spot identified as NSF, which was peptide existing in the C-terminal domain of NSF (amino acids 510-734), underwent a posttranslational modification of cleavage.

(D) With regard to Complexin 1/2, a cerebellum homogenate was separated by a two-dimensional electrophoresis, transcribed from the gel to the PVDF membrane and detected using an anti-Complexin 1/2 antibody whereupon, in MALDI-TOF/MS, not only the spots identified as Complexin 1 and Complexin 2 but also plural spots which were in nearly the same molecular weight and had an isoelectric point in somewhat acidic side were detected and there was a possibility of a posttranslational modification. Although those spots were noted of their changes by analysis of 2D-DIGE, they were not still identified by MALDI-TOF/MS and the spots existing in the same position changes in the mesencephalon as well. In the mesencephalon, concentrations of those spots showed an increase in an acidic side due to SART stress load and such changes were suppressed by administration of a test substance. From the result, it was suggested that the changes of posttranslational modification by SART stress load were found by 2D-DIGE. The above results are summarized in Table 4.

TABLE 4

| Names of Proteins | Mesencephalon | | Cerebellum | |
|---|---|---|---|---|
| | SART | SART + Drug | SART | SART + Drug |
| low MW CRMP-2 | 1.9* | 0.79+ | 0.26* | 0.39 |
| non phospho-CRMP-4 | 0.58* | 0.95+ | | |
| phospho-CRMP-4 | 1.9* | 1.1+ | | |
| low NW Munc-18-1 | 2.9* | 0.94+ | 0.30* | 0.51 |
| Complexin 1/2 | | | 1.6* | 1.4 |
| low pI Complexin 1/2 | 2.0* | 1.1+ | 0.52* | 0.66 |

Calculated as INT = 1
*$p < 0.05$ (vs INT, t-test)
+$p < 0.05$ (vs SART, t-test)

Those which were identified as changing proteins by an expression proteome analysis such as the above CRMP-2, CRMP-4, Munc-18-1 and NSF might be sometimes modified after translation. In the above-mentioned proteins which were confirmed to be changed, some of them are modified after translation while some others are the proteins which were not modified. With regard to the modifying reaction after translation, its examples are an irreversible reaction such as cleavage of peptide chain and addition of sugar chain or fatty acid and a reversible reaction such as acetylation, methylation, hydroxylation, carboxylation, adenylation and ADP ribosylation.

(7) Function of the Identified Protein In Vivo

With regard to the proteins found, information was collected from public databases and known documents.

CRMP-1, CRMP-2 and CRMP-4 are the proteins belonging to the same CRMP family and each of them has not less than 70% of homology. CRMP-2 is a protein participating in elongation of axon and destruction of growth cone and has been reported that the axon elongation is suppressed by phosphorylation. With regard to the CRMP-2 of a cleavage type which was found at this time, although it has been reported to increase with lapse of time after collection of tissues and to decrease in its expression in contracted hippocampus of patients suffering from temporal lobe epilepsy of a medial type, its function and significance in vivo have not been clarified yet. Although CRMP-4 has been known to have the same function as CRMP-2 has, its functional control, etc. have not been known yet and there has been no report for its phosphorylation yet. With regard to the relation between elongation of axon and hyperalgesia, although there has been no direct report therefor, there is a possibility that pain, temperature, etc. cause the changes in nerve network.

Munc-18-1, Complexin 1, Complexin 2, NSF and Synapsin 2 participate in the release of neurotransmitters. Neurotransmitters are stored in secretory vesicles and fused with cell membrane by reacting with stimulation whereupon the release takes place and Munc-18-1, Complexin 1 and Complexin 2 have been known to play an important role in the formation of SNARE complex which is a main protein complex in fusion of secretory vesicles with cell membrane. NSF is also believed to be a protein that participates in SNARE complex and has been clarified to widely operate for the vesicular transport within the cell. With regard to the low-molecular Munc-18-1 which is believed to be a cleavage type, although its function and significance in vivo have not been clarified yet, its existence has been observed in hippocampus and cerebral cortex already.

PGP 9.5 (Protein gene product 9.5; Ubiquitin carboxyl-terminal hydrolase isozyme L1) and alpha synuclein are also proteins which have been known to be specifically expressed in nerves. Although PGP 9.5 is a protein which has been widely used as a marker for nerves, it has a ubiquitin hydrolase activity and is believed to prevent the injury of nerves by yubiquitinization and its disappearance has been known to cause breakage of nerves. Recently, it has been also reported to activate a P2X ATP receptor and to increase the ATP-inductive current. Alpha synuclein is a protein which has been well known to aggregate in Parkinsonism rather than its physiological function and has been reported to suppress the activity of tyrosine phosphorylase participating in dopamine synthesis and to bond to a dopamine transporter whereby flowing of dopamine into cells is decreased.

Besides those nerve-specific proteins, proteins which participate in signal transmission system, cell form, initiation of protein synthesis, energy generation, etc. have been also identified. Known functions of the proteins where the above changes were confirmed and their identifications were done by MALDI-TOF/MS are summarized in Table 5.

TABLE 5

| Names of Proteins | Functions |
|---|---|
| CRMP-2 | Neutrite elongation |
| CRMP-4 | |
| Munc-18-1 | Release of neurotransmitters |
| Complexin 1 | |
| Complexin 2 | |
| Synapsin 2 | |
| NSF | |
| Protein Gene Product 9.5 | Protection and maintenance of nerves |
| Alpha-synuclein | Control of molecular chaperone and enzymatic activity |
| Erk 2 (MAPK) | Cellular signaling |
| Ser/Thr protein kinase PAK 2 | |
| TOLLIP | |
| Actin related protein 2/3 sub 2 | Alteration and movement of cellular morphology |
| Actin related protein 2/3 sub 4 | |
| Tubulin alpha | Constitutive protein for axon and cytoskeleton |
| Regucalcin (SMP 30) | Promotion of uptake of $Ca^{2+}$ |
| eIF5A | for protein synthesis initiation factor |
| Aldehyde dehydrogenase | Mitochondroial enzymes |
| Succinyl CoA ligase | Participating in production of energy |
| Creatine kinase | |
| Ctirate synthase | |
| ATP synthase | |

There is a possibility that the above-mentioned proteins are the causes of abnormal physiological functions such as lowering of pain threshold value in SART stressed animals or the causes of patients suffering from fibromyalgia and that they are target molecules of an extract from inflamed rabbit skin inoculated with vaccinia virus. Accordingly, when changes in those proteins are normalized by a test substance, said test substance has a possibility that it is a drug effective for painful diseases such as fibromyalgia, low back pain, neck-shoulder-arm syndrome, symptomatic neuralgia, periarthritis scapulohumeralis, arthritis deformas and post-herpetic neuralgia, for neuropathic pain such as RSD, abnormal physiological functions by stress, etc.

INDUSTRIAL APPLICABILITY

As mentioned hereinabove, it has been confirmed by the method of the present invention to be able to detect and identify the protein where its expression varies by SART stress load or by administration of an extract from inflamed rabbit skin inoculated with vaccinia virus. Accordingly, the present invention is useful as a method for studying, determining or evaluating a pharmacological action such as an effect on fibromyalgia, an analgesic effect or an antistress effect of a test substance by administering the test substance to a SART stressed animal and then subjecting the brain tissue to an expression proteome analysis.

The invention claimed is:

1. A method for studying, determining or evaluating a pharmacological action of a test substance, the method comprising:
 subjecting the brain tissue of an SART stressed animal administered with the test substance to an expression proteome analysis,
 wherein expression changes of NSF (N-ethylmaleimide sensitive fusion protein), which is or is not modified after translation, in the SART stressed animal administered with the test substance as compared with an SART stressed animal to which a test substance is not administered is used as an index.

2. The method for studying, determining or evaluating according to claim 1, wherein the pharmacological action is an effect to fibromyalgia, an analgesic effect or an antistress effect.

3. The method for studying, determining or evaluating according to claim 1, wherein the SART stressed animal is a rat.

4. The method for studying, determining or evaluating according to claim 1, wherein the brain tissue is mesencephalon, pons or cerebellum.

5. The method for studying, determining or evaluating according to claim 1, wherein the expression proteome analysis uses a fluorescence-labeled two-dimensional differential gel electrophoresis.

6. The method for studying, determining or evaluating according to claim 1, wherein the test substance is an extract from inflamed tissues inoculated with vaccinia virus.

7. The method for studying, determining or evaluating according to claim 6, wherein the test substance is an extract from inflamed rabbit skin inoculated with vaccinia virus.

8. The method according to claim 1, wherein the test substance is a treating agent for fibromyalgia.

9. The method according to claim 1, wherein the test substance is an analgesic agent.

10. The method according to claim 1, wherein the test substance is a drug having an antistress action.

* * * * *